US012741146B2

(12) United States Patent
Guiraud et al.

(10) Patent No.: US 12,741,146 B2
(45) Date of Patent: Sep. 22, 2026

(54) INTRINSICALLY BALANCED NEURAL STIMULATION DEVICE

(71) Applicants: NEURINNOV, Montpellier (FR); CENTRE NATIONAL DE LA RECHERCHE SCIENTIFIQUE—CNRS-, Paris (FR); INRIA—INSTITUT NATIONAL DE RECHERCHE EN INFORMATIQUE ET EN AUTOMATIQUE, Le Chesnay (FR); UNIVERSITÉ DE MONTPELLIER, Montpellier (FR)

(72) Inventors: David Guiraud, Montpellier (FR); David Andreu, Montpellier (FR); Milan Demarcq, Montpellier (FR); Guy Cathebras, Montpellier (FR); Sami Ajram, Simiane-Collongue (FR)

(73) Assignees: NEURINNOV, Montpellier (FR); CENTRE NATIONAL DE LA RECHERCHE SCIENTIFIQUE—CNRS, Paris (FR); INRIA—INSTITUT NATIONAL DE RECHERCHE EN INFORMATIQUE ET EN AUTOMATIQUE, Le Chesnay (FR); UNIVERSITÉ DE MONTPELLIER, Montpellier (FR)

( * ) Notice: Subject to any disclaimer, the term of this patent is extended or adjusted under 35 U.S.C. 154(b) by 363 days.

(21) Appl. No.: 18/294,297

(22) PCT Filed: Jul. 29, 2022

(86) PCT No.: PCT/FR2022/051523

§ 371 (c)(1),
(2) Date: Feb. 1, 2024

(87) PCT Pub. No.: WO2023/012422

PCT Pub. Date: Feb. 9, 2023

(65) Prior Publication Data

US 2024/0342481 A1 Oct. 17, 2024

(30) Foreign Application Priority Data

Aug. 3, 2021 (FR) ...................................... 2108450

(51) Int. Cl.
*A61N 1/36* (2006.01)

(52) U.S. Cl.
CPC ................................ *A61N 1/36125* (2013.01)

(58) Field of Classification Search
CPC .............................. A61N 1/36; A61N 1/36125
See application file for complete search history.

(56) References Cited

U.S. PATENT DOCUMENTS 5,769,877 A * 6/1998 Barreras, Sr. ...... A61N 1/37223 607/61
2011/0125224 A1 5/2011 Carbunaru et al.
(Continued)

FOREIGN PATENT DOCUMENTS

EP 3100766 A1 12/2016
WO 2006027473 A1 3/2006

OTHER PUBLICATIONS

International Search Report issued on Nov. 4, 2022, in corresponding International Patent Application No. PCT/FR2022/051523, 8 pages.

*Primary Examiner* — George Manuel
(74) *Attorney, Agent, or Firm* — Maier & Maier, PLLC

(57) ABSTRACT

A current switcher including: a positive supply bus and a negative supply bus; a floating-output current amplifier configured to make flow, as an output, an intermediate current dependent on a flowing setpoint current implied as an input; at least one anodic reference dipole connected between the positive supply bus and the floating-output
(Continued)

current amplifier; at least one cathodic reference dipole connected between the floating-output current amplifier and the negative supply bus; and at least two stimulation bridges, each stimulation bridge including an anodic current source and a cathodic current source each configured to copy the intermediate current.

20 Claims, 4 Drawing Sheets

(56) References Cited

U.S. PATENT DOCUMENTS

2019/0328565 A1* 10/2019 Perez ................ A61N 1/36017
2020/0016415 A1 1/2020 Perryman et al.
2020/0179702 A1 6/2020 Lee

* cited by examiner

INTRINSICALLY BALANCED NEURAL STIMULATION DEVICE

FIELD

The present invention relates to a current switcher for a neural stimulation current distributor.

The invention also relates to a neural stimulation current distributor comprising such a current switcher, a medical device comprising such a current distributor, a neuro-stimulation system comprising such a medical device and a neuro-stimulation method.

The invention applies to the field of functional electrical stimulation.

BACKGROUND

Functional electrical stimulation is a technique intended to provoke, inhibit, or modulate a nervous message.

To do this, neural electrodes, such as stimulation electrodes applied around a nerve (gutter electrode, or "cuff" in English) or across the nerve (LIFE type intrafascicular electrode, from English "Longitudinal Intrafascicular Electrode" or TIME, from the English "transverse intrafascicular multichannel electrode"), are used to circulate an electrical current, in particular an electrical impulse, through the nerve, thus causing generation (depolarization) or blockage (hyperpolarization) of axonal action potentials. This method can be generalized without difficulty to the stimulation of any nervous tissue, whether cerebral or spinal for example.

The aim of this neural stimulation is to activate all or part of the nerve by injecting anodic or cathodic currents at the level of the neural electrodes. More precisely, during a first phase of operation, called "stimulating", the injection of a current into the nerve, comparable to an injection of charges, through at least two electrodes, results in a movement of ions causing the appearance of an action potential in the nerve.

It is considered, by way of example, a medical neuro-stimulation device, presenting a simplified configuration with two electrode contacts intended for stimulation, as well as a reference contact serving as a potential reference.

In FIG. 1, the current delivered during the stimulating phase is represented, by way of example, by a first slot starting at a time $t_1$, of amplitude A and duration $\tau_1$.

In this simplified configuration, this means that the incoming current slot of amplitude A on the first contact corresponds to a simultaneous outgoing current slot of the same amplitude A on the second contact.

Then, during a second phase of operation, subsequent to the first, the local electrical balance of the nerve is restored. For example, this second operating phase implements active balancing, by recovering loads in the environment, following a predetermined time profile. This profile is such that the quantity of charges recovered, cumulative over the duration of the second phase, is of opposite value to that injected during the stimulating phase.

In this same FIG. 1, the current generated during this second phase is represented by a second slot starting at a time $t_2$, of amplitude −B, and of duration $\tau_2$.

In this simplified configuration, this means that the outgoing current slot of amplitude B on the first contact corresponds to a simultaneous incoming current slot of the same amplitude B on the second contact.

In most applications, the amplitudes A and B are equal, as are the durations $\tau_1$ and $\tau_2$. In this way, a total quantity of injected charges that is globally zero over all of the two phases is guaranteed, in theory.

More generally, there can be several phases and several profile shapes, but the constraint specifying that, overall, the quantity of charges injected per stimulus is equal to zero remains.

For example, document WO 200627473 A1 proposes a medical device comprising a current distributor intended to produce such currents.

However, such a medical device does not give complete satisfaction.

Indeed, such a current distributor is subject to mismatches of the anodic and cathodic currents. Such errors arise, among other things, from errors in routing the reference current to the cathode and anode current sources, errors which are not strictly identical by construction.

In FIG. 2-A, and in the simplified example with two stimulation contacts and a reference contact mentioned above, these errors are illustrated by a difference in amplitude, in absolute value, between the outgoing current burst at level of the first contact (solid line) and the current window entering simultaneously at the level of the second contact (dashed line).

In this situation, the difference between the current entering the first stimulation contact and the current leaving the second stimulation contact is absorbed by the reference contact. This therefore implies, firstly, that the current is not delivered in accordance with an expected set current and that the spatial distribution of the current in the nerve is not the desired one (current leakage towards the reference contact).

Secondly, due to this error, the second opposite stimulation phase (subsequent to the stimulating phase, as described previously in connection with FIG. 1) cannot lead to a balance of charges on the different contacts.

The current error between cathodic and anodic current sources is also related to the difference in current stabilization dynamics, which can induce large relative errors at short pulse widths.

In FIG. 2-B, and in the simplified example with two stimulation contacts and a reference contact mentioned above, such errors are illustrated by a difference in slope between, on the one hand, the rising and falling edges of a current slot entering at the level of the first contact (continuous line) and, on the other hand, the rising and falling edges of a corresponding slot leaving simultaneously at the level of the second contact (dashed line).

In this situation also, the difference (at transition times) between current incoming on the first contact and outgoing current on the second contact is absorbed by the reference contact. This therefore leads, in a manner analogous to the situation in FIG. 2-A, to a difference between set current and actually injected current. The quantity of charge injected and recovered on the two stimulation contacts is also not the same; the theoretical rebalancing of loads is therefore all the less precise.

As an illustration, the evolution of the error (solid line) between incoming current on the first contact and outgoing current on the second contact in the situations of FIGS. 2A and 2B is illustrated by FIGS. 3-A and 3-B respectively. In the configuration with two stimulation contacts and one reference contact, this error corresponds to the current absorbed by the reference contact. The integral of this error over time is also represented (dashed line).

If we place ourselves in another simplified stimulation configuration, comprising only two stimulation contacts without reference contact, the situation is slightly different but the final problems remain. Indeed, during the unbalanced stimulations illustrated in FIG. 2, the difference between current entering the first contact and current leaving the second contact is not absorbed by another reference contact and it is therefore the contact for which the absolute current value is the lowest which imposes the value of the incoming and outgoing currents. This type of situation therefore leads to undesired saturation of the current sources and an unknown current actually delivered. Finally, during a second phase intended to balance the loads on the two contacts, the second current slot, whose absolute setpoint amplitude is equal to that of the first slot, will present the same fault and its real amplitude will be unknown and therefore potentially different from the opposite of the amplitude of the first slot. This situation also results in an impossibility of balancing the charges injected and recovered on the different contacts.

Overall, this has a direct and significant impact on the problems mentioned above. Indeed, such errors induce not only imprecision in the distribution between incoming and outgoing currents, essentially at low amplitudes, which can degrade selectivity performance, but also uncertainty in the quantity of charges injected, particularly at high amplitudes, which can induce a significant imbalance. More precisely, an unknown residual charge, equal to the difference between the integrals of the outgoing and incoming currents, is indeterminate, and cannot therefore be intrinsically compensated by supposedly perfect operating phases.

Although capacitive coupling at the level of the contacts allows, through a passive discharge, a rebalancing of the charges, a significant error from this imbalance requires making this discharge more frequent (and therefore limiting the stimulation frequency). In addition, each discharge is likely to include larger current peaks that can induce undesired or suboptimal effects.

However, the current switcher of the state of the art does not integrate characteristics allowing correction of this defect by construction, that is to say intrinsically.

Although the simplified stimulation configurations described above are bipolar configurations (two stimulation contacts, with/without reference), this phenomenon is also present and its consequences are even more pronounced and problematic in a multipolar stimulation context (multiple contacts delivering outgoing currents and several contacts delivering incoming currents, simultaneously), which is generally the context of selective stimulation.

An aim of the invention is therefore to propose a current switcher for a neural stimulation current distributor presenting a lower risk of damage to the nerves, while having a simple architecture.

SUMMARY

To this end, the subject of the invention is a current switcher of the aforementioned type, comprising:

- a positive power bus intended to be connected to a positive power source, and a negative power bus intended to be connected to a negative power source;
- a current amplifier with floating output comprising, on the one hand, a primary input terminal and a primary output terminal, and, on the other hand, a secondary input terminal and a secondary output terminal, the floating output current amplifier being configured to circulate, between the secondary input terminal and the secondary output terminal, an intermediate current depending on a set current circulating between the terminal primary input and primary output terminal;
- at least one anodic reference dipole comprising an anodic current input connected to the positive power bus and an anodic current output connected to the secondary input terminal of the floating output current amplifier;
- at least one cathode reference dipole comprising a cathodic current input connected to the secondary output terminal of the floating output current amplifier, and a cathodic current output connected to the negative power bus; and
- at least two stimulation bridges, each stimulation bridge comprising:
  - a stimulation port;
  - an anodic current source connected between the positive power bus and the stimulation port, and configured to copy, with a respective anodic gain, the intermediate current passing through an associated anodic reference dipole among the at least one anodic reference dipole; and
  - a cathodic current source connected between the stimulation port and the negative power bus, and configured to copy, with a respective cathode gain, the intermediate current passing through an associated cathode reference dipole among the at least one cathode reference dipole.

Indeed, thanks to such an architecture, the generation of a precise and balanced stimulus is made possible. In other words, the delay and the amplitude error between the current leaving through a first contact and the current entering through a second corresponding contact is greatly reduced, and this intrinsically. The risk of load accumulation in the nerve is therefore also reduced. The result is a safer neurostimulation system.

Furthermore, the use of such a stimulation current distributor simplifies the design of an implantable stimulation device incorporating the current distributor, to the extent that the integration of circuits intended to compensate, for each stimulation channel, of any delays are not to be expected. It follows that the compactness of such stimulation device is also improved.

The invention also applies to a configuration with several contacts, each connected to a corresponding stimulation port. In this case, a synchronous distribution of currents on part or all of the contacts of the electrode makes it possible to more particularly target an area of the nerve, what is called selective stimulation.

According to other advantageous aspects of the invention, the current switcher comprises one or more of the following characteristics, taken in isolation or in all possible technical combinations:

- the current amplifier with floating output is a current-balanced non-reciprocal quadrupole configured so that the intermediate current is connected to the set current by a relation of proportionality, preferably by the relation:

$$\begin{pmatrix} V_1 \\ I_2 \end{pmatrix} = \begin{pmatrix} H_{11} & 0 \\ H_{12} & 0 \end{pmatrix} \begin{pmatrix} I_1 \\ V_2 \end{pmatrix}$$

where $V_1$ is a voltage between the primary input terminal and the primary output terminal; $V_2$ is a voltage between the secondary input terminal and the secondary output terminal;

- $I_1$ is the set current;
- $I_2$ is the intermediate current;
- $H_{11}$ is a first predetermined coefficient, homogeneous with a resistance; and
- $H_{12}$ is a second predetermined, dimensionless coefficient.

the current amplifier with floating output comprises at least one current conveyor comprising a current input port, a voltage input port and a current output port, the current conveyor being, preferably, a second generation current conveyor presenting an operation governed by the relationship:

$$\begin{pmatrix} I_Y \\ V_X \\ I_Z \end{pmatrix} = \begin{pmatrix} 0 & 0 & 0 \\ 1 & 0 & 0 \\ 0 & -1 & 0 \end{pmatrix} \begin{pmatrix} V_Y \\ I_X \\ V_Z \end{pmatrix}$$

where $I_X$, $I_Y$ and $I_Z$ are respectively currents injected into the input port of current, voltage input port and current output port; and $V_X$, $V_Y$ and $V_Z$ are voltages between, on the one hand, respectively, the current input port, the voltage input port and the current output port, and, on the other hand, a reference point having a predetermined electric potential;

each current conveyor is a metal-oxide gate field effect transistor whose source forms the current input port, the gate forms the voltage input port and the drain forms the current output port;

the current amplifier with floating output comprises a first current conveyor, a second current conveyor, a third current conveyor and a fourth current conveyor, the first current conveyor and the second current conveyor being identical, the third current conveyor and the fourth current conveyor being identical, the current input port of the first current conveyor being connected to the current input port of the fourth current conveyor, the current input port of the second current conveyor current being connected to the current input port of the third current conveyor, the current output port of the first current conveyor, the voltage input port of the first current conveyor and the voltage input port of the second current conveyor being connected to each other, the current output port of the fourth current conveyor, the voltage input port of the fourth current conveyor and the voltage input port of the third current conveyor being connected to each other, the current output port of the first current conveyor being connected to the primary input terminal of the floating output current amplifier, the current output port of the fourth current conveyor being connected to the primary output terminal of the floating output current amplifier, the current output port of the second current conveyor being connected to the secondary input terminal of the floating output current amplifier, and the current output port of the third current conveyor current being connected to the secondary output terminal of the floating output current amplifier;

the floating output current amplifier comprises a first current conveyor, a second current conveyor and a third current conveyor, the current input port of the first current conveyor being connected to the port voltage input port of the third current conveyor, the current output port of the first current conveyor, the voltage input port of the first current conveyor and the voltage input port of the second current conveyor being connected between them, the current input port of the second current conveyor being connected to the current input port of the third current conveyor, the current output port of the first current conveyor, the voltage input port of the first current conveyor and the voltage input port of the second current conveyor being connected to each other, the first predetermined coefficient $H_{11}$ being worth 0, the second predetermined coefficient $H_{12}$ being worth 1, and:

the current output port of the first current conveyor being connected to the primary input terminal of the floating output current amplifier, the voltage input port of the third current conveyor being connected to the primary the current output port of the second current conveyor being connected to the secondary input terminal of the floating output current amplifier, and the current output port of the third current conveyor being connected to the secondary output terminal of the floating output current amplifier, or:

the voltage input port of the third current conveyor being connected to the primary input terminal of the current amplifier with floating output, the current output port of the first current conveyor being connected to the primary output terminal of the floating output current amplifier, the current output port of the third current conveyor being connected to the secondary input terminal of the floating output current amplifier, and the current output port of the second current conveyor being connected to the secondary output terminal of the floating output current amplifier;

the current switcher also includes a reference terminal intended to be connected, on the one hand, between the positive power source and the negative power source, and, on the other hand, to a potential reference, the reference terminal being, in addition, connected to the anodic current output of each anodic reference dipole by a respective anodic load, and to the current input cathode of each cathode reference dipole by a respective cathode charge;

for each stimulation bridge:

the corresponding anodic reference dipole comprises a first anode transistor, and the corresponding anodic current source comprises at least a second anode transistor, each second anode transistor being connected to the first anode transistor to define, with the first anode transistor, a mirror of current; and the corresponding cathode reference dipole comprises a first cathode transistor, and the corresponding cathodic current source comprises at least a second cathode transistor, each second cathode transistor being connected to the first cathode transistor to define, with the first cathode transistor, a mirror of current;

for each stimulation bridge:

the corresponding anodic current source comprises at least one anodic elementary source connected between the positive power supply bus and the stimulation port, each anodic elementary source comprising a second anode transistor in series with an anodic switching member; and/or the corresponding cathodic current source comprises at least one cathodic elementary source connected between the stimulation port and the negative power supply bus, each cathodic elementary source comprising a second cathode transistor in series with a cathodic switching member, the value of the gain anodic being a function of an on or off state of each anodic switching member, and/or the value of the cathodic gain being a function of an on or off state of each cathodic switching member;

for each stimulation bridge:

- the corresponding anodic current source comprises a plurality of elementary anode sources connected in parallel between the positive power bus and the stimulation port; and/or
- the corresponding cathodic current source comprises a plurality of elementary cathode sources connected in parallel between the stimulation port and the negative power bus.

Furthermore, the subject of the invention is a neural stimulation current distributor comprising a current switcher as defined above, and a programmable current generator connected between the primary input terminal and the primary output terminal of the current amplifier with floating output, the programmable current generator being configured to deliver the set current according to a command applied to it.

Furthermore, the subject of the invention is an implantable medical device comprising a neural stimulation current distributor as defined above, a sequencer, and a plurality of contacts each connected to a respective stimulation port, the sequencer being configured to control, according to a received command sequence associated with a corresponding neurostimulation, each anodic current source, respectively each cathodic current source, to fix the value of the corresponding anodic gain, respectively of the corresponding cathodic gain, so that, at every moment:

- for each stimulation bridge, one of the corresponding anodic gain and cathodic gain is zero; and
- the sum of the anodic gains and the sum of the cathodic gains, taken over all the stimulation bridges, are equal.

According to other advantageous aspects of the invention, the implantable medical device comprises one or more of the following characteristics, taken in isolation or in all possible technical combinations:

- the implantable medical device further comprises a receiver connected to the input of the sequencer, the receiver being configured to receive, preferably via a wireless link, the command sequence, and to transmit the received command sequence to the sequencer;
- the sequencer is configured to control each anodic current source and each cathodic current source, as a function of the set current, so that:
  - the integral of a total current flowing between the positive power bus and the negative power bus during a stimulation time window is equal to the integral of the total current during a time window of return to equilibrium, the stimulation time window and the return to equilibrium time window being consecutive and distinct from each other; and
  - the anodic gain of at least one anodic current source, respectively the cathodic gain of at least one cathodic current source, has a zero value during one of the stimulation time window and the return to point time window balance, and a non-zero value during the other among the stimulation time window and the return to equilibrium time window;
- the sequencer is, in addition, configured to control the programmable current generator in order to deliver the set current according to the command sequence received;
- for each stimulation bridge:
  - the corresponding anodic current source comprises at least one anodic elementary source connected between the positive power supply bus and the stimulation port, each anodic elementary source comprising a second anode transistor in series with an anodic switching member; and/or
  - the corresponding cathodic current source comprises at least one cathodic elementary source connected between the stimulation port and the negative power supply bus, each cathodic elementary source comprising a second cathode transistor in series with a cathodic switching member, the sequencer being configured to control, depending on the command sequence, an on or off state of each anodic switching member to set the value of the anodic gain, and/or to control an on or off state of each cathodic switching member to set the value of the cathode gain.

Furthermore, the subject of the invention is a neurostimulation system comprising an implantable medical device as defined above and a controller configured to determine each command sequence, and to transmit each determined command sequence to the implantable medical device, preferably via a wireless connection.

Furthermore, the subject of the invention is a neurostimulation method implemented by means of the implantable medical device as defined above, the neurostimulation method comprising the steps:

- during a stimulation time window, injection of the set current between the primary input terminal and the primary output terminal of the current amplifier with floating output, the anodic gain of at least a first bridge of stimulation being non-zero, and the cathodic gain of at least a second stimulation bridge being non-zero; and
- during a time window of return to equilibrium, injection of the set current between the primary input terminal and the primary output terminal of the current amplifier with floating output, the anodic gain of at least a third stimulation bridge being non-zero, and the cathodic gain of at least a fourth stimulation bridge being non-zero, the integral of a total current circulating between the positive power bus and the negative power bus during the stimulation time window being equal to the integral of the total current during the time window of return to equilibrium, the time window of stimulation and the time window of return to equilibrium being consecutive and distinct the one from the other.

BRIEF DESCRIPTION OF THE DRAWINGS

The invention will be better understood with the help of the description which follows, given solely by way of non-limiting example and made with reference to the appended drawings in which.

DETAILED DESCRIPTION

Figure 1:
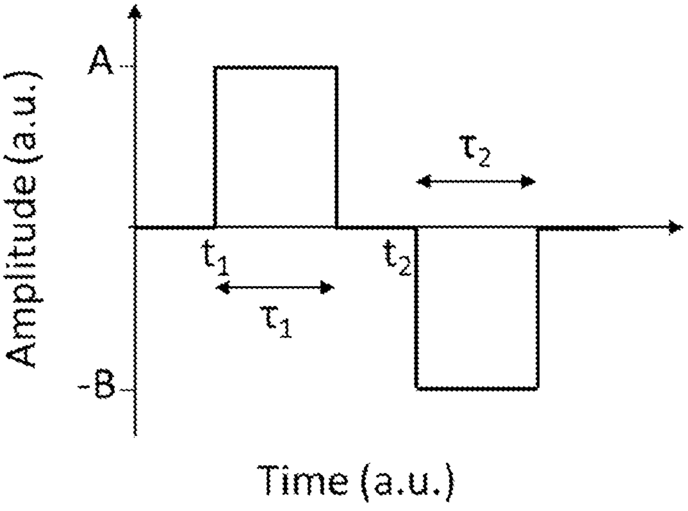
FIG. 1 this figure is a graph representing a temporal profile of symmetrical biphasic stimulation.
Figure 2:
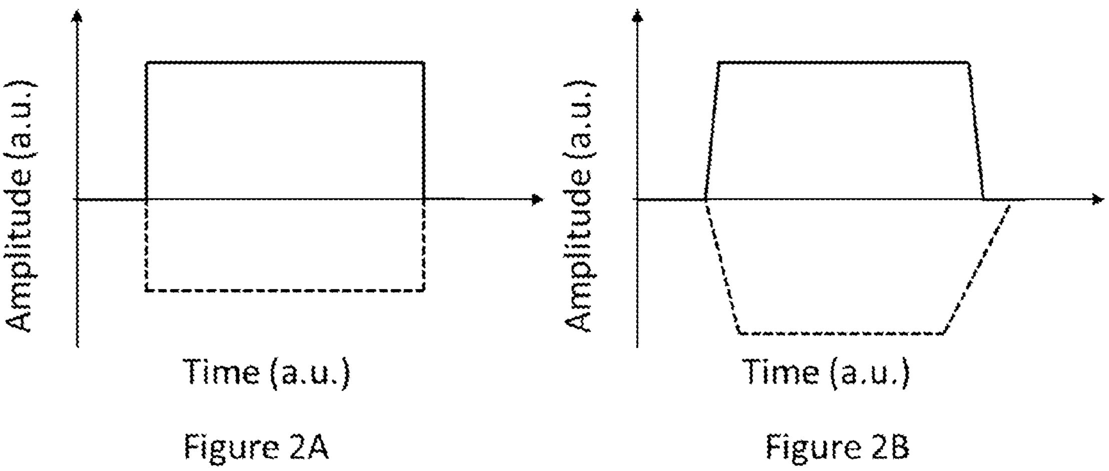
FIG. 2: A is a graph representing the evolution, over time, of currents incoming and outgoing on two contacts of a neuro-stimulation system of the state of the art, and illustrating a copying error; in addition, B is a graph representing the evolution, over time, of currents entering and leaving on two contacts of a neuro-stimulation system of the state of the art, and illustrating an error of deadline.
Figure 3:
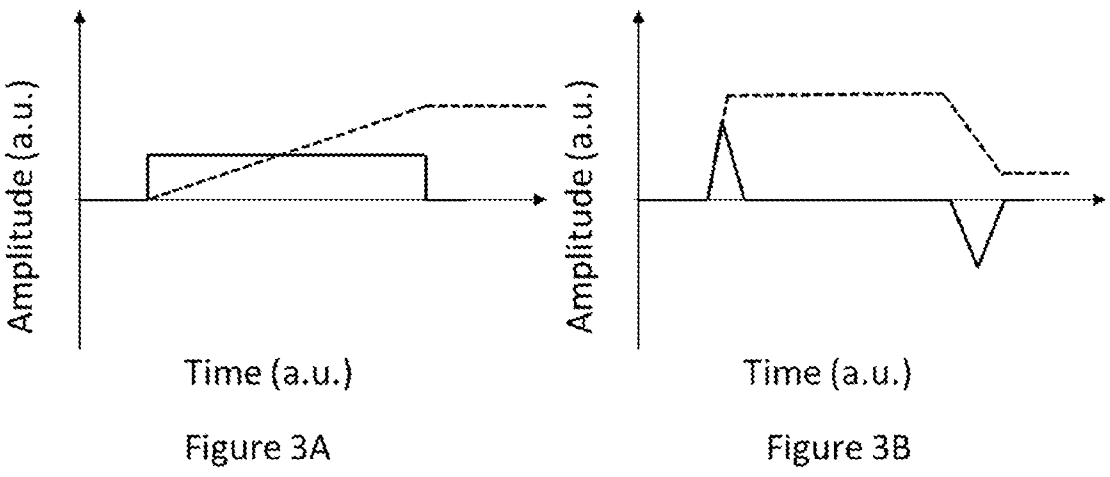
FIG. 3: A is a graph representing the evolution, over time, of an error between a current entering on a first contact and a current leaving on a second contact of a neuro-stimulation system of the state of the art, as well as the integral of this error, caused by the copying error of FIG. 2-A; in addition, B is a graph representing the evolution, over time, of an error between the current entering on the first contact and the current leaving on the second contact of the neuro-stimulation system of the state of the art, as well as the integral of this error, caused by the delay error of FIG. 2-B.
Figure 4:
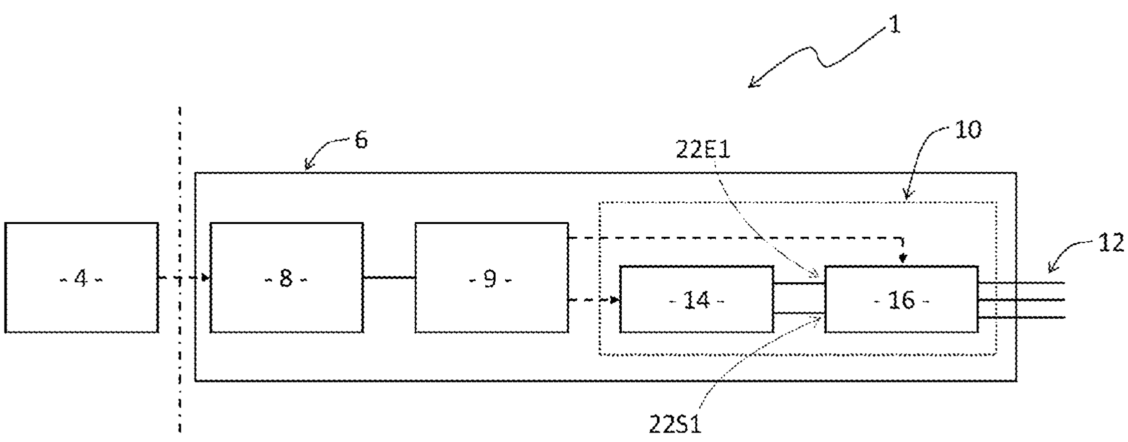
FIG. 4 is a schematic representation of a neurostimulation system according to the invention.

A neurostimulation system 1 according to the invention is illustrated in FIG. 4. Such a neurostimulation system is intended for the implementation of functional electrical stimulation (also called "neurostimulation") in a patient.

As appears in FIG. 4, the neuro-stimulation system 1 comprises a controller 4 and an implantable medical device 6 configured to cooperate together in order to ensure the neurostimulation function.

More precisely, the controller 4 is configured to determine a plurality of command sequences as a function of a targeted neurostimulation, and to transmit each command sequence to the implantable medical device 6, in order to control the operation of the implantable medical device. 6. As will become apparent from the rest of this description, such sequences relate to profiles of anodic gains, cathodic gains and set current to be implemented to achieve, for example, a predetermined motor function.

Such command sequences are intended to be translated, by the implantable medical device 6, into electrical impulses aimed at causing, inhibiting or modulating one or more nervous message(s) in the patient, in particular with a view to controlling a motor function of the patient. In other words, the implantable medical device 6 is configured to deliver electrical impulses to one or more nerves of the patient based on the sequences received from the controller 4.

Advantageously, the controller 4 and the implantable medical device 6 are configured to communicate with each other via a wireless link.

To ensure the autonomy of the patient, the controller 4 is preferably a portable device, for example a smartphone, having minimal bulk and weight. In this way, the patient is able to carry the controller 4 permanently with him.

The implantable medical device 6 is intended to be implanted, in the body of the patient, and to interface with one or more nerves thereof, according to methods known in the field of the invention.

The implantable medical device 6 comprises a receiver 8, a sequencer 9 connected to the receiver 8, a neural stimulation current distributor 10 (also called "current distributor" hereinafter) connected to the sequencer 9, and a plurality of contacts 12 each connected to current distributor 10.

The receiver 8 is configured to receive the command sequences from the controller 4, and to transmit the sequences received to the sequencer 9. Preferably, the receiver is configured to receive the command sequence via a wireless connection through the patient's skin, represented in FIG. 4 by a dashdotted line.

The sequencer 9 is configured to control the current distributor 10 according to each command sequence received.

In addition, the current distributor 10 is configured to apply to the contacts 12 electrical currents whose temporal profile depends on the control carried out by the sequencer 9, and which is a function of the command sequence provided by the controller 4. Finally, the contacts 12 are contacts conventionally known in the field of the invention, and can be grouped into one or more stimulation electrodes (not shown).

A detailed description of the sequencer 9 will be given later, once the current distributor 10 has been described.

As illustrated in FIG. 4, the current distributor 10 comprises a programmable current generator 14 (also called "generator") and a current switcher 16 connected to the output of the generator 14.

The generator 14 is configured to deliver a set current, according to a command carried out by the sequencer 9.

Figure 5:
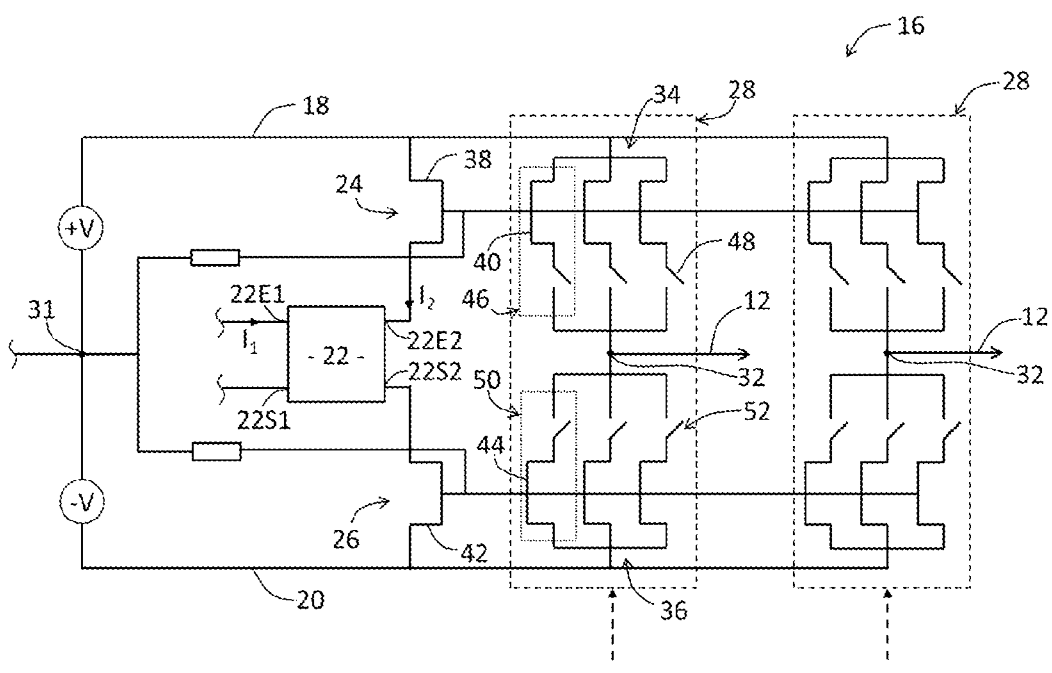
FIG. 5 is a schematic representation of a current distributor of the neurostimulation system of FIG. 4.

In addition, the current switcher 16, the architecture of which will now be described with reference to FIG. 5, is intended for shaping and switching the current pulses supplied by the generator 14.

Architecture of the Current Switcher 16

The current switcher 16 includes a positive power bus 18 and a negative power bus 20. The current switcher 16 also comprises a current amplifier 22 with floating output, at least one anodic reference dipole 24, at least one cathode reference dipole 26. In addition, the current switcher 16 comprises at least two stimulation bridges 28.

Preferably, the current switcher 16 also includes a reference terminal 31.

Power Bus

The positive power bus 18 is intended to be connected to a positive power source. Furthermore, the negative power bus 20 is intended to be connected to a negative power source.

Current Amplifier

The current amplifier 22 is configured to deliver an intermediate current dependent on a current applied to it as input. The current amplifier 22 comprises, on the one hand, a primary input terminal 22E1 and a primary output terminal 22S1. The generator 14 is connected between this primary input terminal 22E1 and this primary output terminal 22S1, so that the current applied to the input of the current amplifier 22 is the set current delivered by the current generator 14.

The current amplifier 22 also comprises a secondary input terminal 22E2 and a secondary output terminal 22S2. More precisely, the current amplifier 22 is configured to circulate, between its secondary input terminal 22E2 and its secondary output terminal 22S2, said intermediate current when the set current flows between its primary input terminal 22E1 and its primary output terminal 22S1.

The current amplifier 22 is preferably a non-reciprocal current-balanced quadrupole.

Advantageously, the current amplifier 22 is configured so that the intermediate current is equal to the product of the set current by a current amplifier gain $H_{12}$. For example, in the case where the current amplifier 22 is a current-balanced non-reciprocal quadrupole, the current amplifier 22 is configured so that the intermediate current is connected to the set current by the relation:

$$\begin{pmatrix} V_1 \\ I_2 \end{pmatrix} = \begin{pmatrix} H_{11} & 0 \\ H_{12} & 0 \end{pmatrix} \begin{pmatrix} I_1 \\ V_2 \end{pmatrix}$$

where $V_1$ is a voltage between the primary input terminal 22E1 and the primary output terminal 22S1;

$V_2$ is a voltage between secondary input terminal 22E2 and secondary output terminal 22S2;

$I_1$ is the set current;

$I_2$ is the intermediate current;

$H_{11}$ is a first predetermined coefficient, homogeneous with a resistance; and $H_{12}$ is a second predetermined, dimensionless coefficient, previously called "current amplifier gain".

Alternatively, the relationship between the set current and the intermediate current is an affine relationship. In the latter case, the current switcher 16 also includes a member for compensating the quiescent current of the current amplifier 22.

A detailed description of the architecture of the current amplifier 22 will be provided later.

Reference Dipoles

The anodic reference dipoles 24 and the cathode reference dipoles 26 are intended to provide, at any instant, two identical, synchronous copies of the intermediate current which flows between the secondary input terminal 22E2 and the secondary output terminal 22S2 of the current amplifier 22.

More precisely, each anodic reference dipole 24 comprises an anodic current input 24E connected to the positive power bus 18 and an anodic current output 24S connected to the secondary input terminal 22E2 of the current amplifier 22. Furthermore, each cathode reference dipole 26 includes a cathodic current input 26E connected to the secondary output terminal 22S2 of the current amplifier 22, and a cathodic current output 26S connected to the negative power bus 20.

In this way, the intermediate current is able to flow from the positive power bus 18 to the negative power bus 20, through each anodic reference dipole 24 to the current amplifier 22, then through each cathode reference dipole 26, and this as a function of the set current circulating between the primary input terminal 22E1 and the primary output terminal 22S1 of the current amplifier 22.

Such a current switcher 16 is therefore such that the time profile of a first intermediate current circulating in the branch between the positive power supply bus 18 and the secondary input terminal 22E2 is identical to the time profile of a second intermediate current circulating in the branch between the secondary output terminal 22S2 and the negative power bus 20. As a result, the addition of circuits intended to compensate for possible delays between these two branches is not to be expected.

Stimulation Bridges

Each stimulation bridge 28 comprises a stimulation port 32 electrically connected to a respective contact 12, an anodic current source 34 associated with a corresponding anodic reference dipole 24, as well as a cathodic current source 36 associated with a corresponding cathodic reference dipole 26.

More precisely, for each stimulation bridge 28, the anodic current source 34 is connected between the positive power bus 18 and the stimulation port 32. Symmetrically, the cathodic current source 36 is connected between the stimulation port 32 and the negative power bus 20.

In addition, each anodic current source 34 is configured to copy, with a respective anodic gain $K_a$, the intermediate current passing through the associated anodic reference dipole 24. In the same way, each cathodic current source 36 is configured to copy, with a respective cathode gain $K_c$, the intermediate current passing through the associated cathode reference dipole 26. The values of the anodic gains $K_a$ and cathodic gains $K_c$ are variable, as will emerge from what follows.

Preferably, and as appears in FIG. 5, for each stimulation bridge 28, the corresponding anodic current source 34 comprises at least one second anode transistor 40. In this case, the corresponding anodic reference dipole 24 comprises a first anode transistor 38, each second anode transistor 40 being connected to the first anode transistor 38 to define, with the latter, a current mirror.

Similarly, for each stimulation bridge 28, the corresponding cathodic current source 36 preferably comprises at least one second cathode transistor 44. In this case, the corresponding cathode reference dipole 26 comprises a first cathode transistor 42, each second cathode transistor 44 being connected to the first cathode transistor 42 to define, therewith, a current mirror.

Due to such a symmetrical architecture, undesirable phase shifts between the anodic current sources 34 and the cathodic current sources 36 inserted in the circuit, during the operation of the neuro-stimulation system 1, are avoided. For the same reasons, differences in behavior between these two current sources 34, 36 (for example disparities in the current establishment times) are also avoided, in particular if identical electronic components are used.

Preferably, each second anode transistor 40 is integrated into an elementary anode source 46 connected between the positive power supply bus 18 and the stimulation port 32. Such an elementary anode source 46 comprises the second anode transistor 40 in series with an anodic switching member 48 capable of switching between an on state and a blocked state.

More preferably, each second cathode transistor 44 is integrated into an elementary cathode source 50 connected between the stimulation port 32 and the negative power bus 20. Such an elementary cathode source 50 comprises the second cathode transistor 44 in series with a cathodic switching member 52 also capable of switching between an on state and a blocked state.

In this way, each elementary anode source 46 (respectively cathodic 50) is caused to copy or not the intermediate current passing through the reference dipole anodic 24 (respectively cathodic 26) associated with the corresponding anodic current source 34 (respectively cathodic 36), depending on a state of its anodic switching member 48 (respectively cathodic 52).

Advantageously, for each stimulation bridge 28, the corresponding anodic current source 34 comprises a plurality of anodic elementary sources 46 connected in parallel between the positive power supply bus 18 and the stimulation port 32. Similarly, for each stimulation bridge 28, the corresponding cathodic current source 36 advantageously comprises a plurality of elementary cathode sources 50 connected in parallel between the stimulation port 32 and the negative power bus 20.

This is advantageous, insofar as the selective control of the on or off state of each anodic switching member 48 (respectively cathodic 52) of a given anodic current source 34 (respectively cathodic 36) authorizes a modification, in time, of the value of the gain $K_a$ of said anodic current source 34 (respectively of the gain $K_c$ of said cathodic current source 36).

Sequencer 9

The organs of the current distributor having now been described, a detailed description of the sequencer 9 will now be provided.

As indicated previously, the sequencer 9 is configured to control the current distributor 10 according to each command sequence received.

More precisely, the sequencer 9 is intended to control the value of the gain of each anodic current source 34 and each cathodic current source 36 of the current switcher 16, as a function of the command sequence received from the controller 4, and this so as to provide, to each contact 12, a current conforming to a neurostimulation to be carried out corresponding to said command sequence.

The sequencer 9 is also configured to control the programmable current generator 14 so that said programmable current generator 14 delivers the set current according to the command sequence received from the controller 4.

More precisely, the sequencer 9 is configured to control, depending on the command sequence received from the controller 4, each anodic current source 34 to set the value of the corresponding anodic gain $K_a$, and each cathodic current source 36 to set the value of the corresponding cathodic gain $K_c$.

For reasons of balance of quantity of charges, such a command requires that at each moment, the following conditions are met:

- for each stimulation bridge 32, one of the corresponding anodic gain $K_a$ and cathodic gain $K_c$ is zero; and
- the sum of the anodic gains $K_a$, taken over all the stimulation bridges 32, is equal to the sum of the cathodic gains $K_c$, also taken over all the stimulation bridges 32.

In this way, at any time, the sum of the currents going out to the patient is equal to the sum of the currents entering from the patient, so that leakage currents are avoided.

Advantageously, in the case where at least one anodic current source 34 comprises a plurality of elementary anode sources 46 as described above, the sequencer 9 is configured to control an on or off state of each corresponding anodic switching member 48 to set the value of the anodic gain Ka. More precisely, for the anodic current source 34 considered, the anodic gain $K_a$ may take several values between 0 and a respective maximum anodic gain, depending on the number of anodic switching members 48 in an on-state.

Furthermore, if an anodic current source 34 comprises a single anodic elementary source 46, the anodic gain $K_a$ is equal to either 0 or the respective maximum anodic gain, depending on the on or off state of the anodic switching member 48.

Similarly, in the case where at least one cathodic current source 36 comprises a plurality of elementary cathode sources 50 as described above, the sequencer 9 is configured to control an on or off state of each corresponding cathodic switching member 52 to set the value of the cathodic gain $K_c$. More precisely, for the cathodic current source 36 considered, the cathode gain $K_c$ may take several values between 0 and a maximum cathode gain, depending on the number of cathodic switching members 52 in an on state.

Furthermore, if a cathodic current source 36 comprises a single elementary cathode source 50, the cathode gain Kc is equal to either 0 or the respective maximum cathode gain, depending on the on or off state of the cathodic switching member 52.

According to another advantageous aspect, the sequencer 9 is configured to control each anodic current source 34 and each cathodic current source 36, as a function of the value of the set current, so that:

- the integral of a total current circulating between the positive power bus 18 and the negative power bus 20 during a stimulation time window is equal to the integral of the total current during a time window for return to equilibrium, the stimulation time window and the time window for return to equilibrium being consecutive and distinct from each other; and
- the anodic gain $K_a$ of at least one anodic current source 34, respectively the cathodic gain $K_c$ of at least one cathodic current source 36, has a zero value during one of the stimulation time window and the time window for return to equilibrium, and a non-zero value during the other among the stimulation time window and time window for return to equilibrium.

In this way, all local charges created during the stimulation time window are canceled during the return to equilibrium time window.

Reference Terminal

Reference terminal 31 is intended to be connected between the positive power source and the negative power source.

In addition, the reference terminal 31 is connected to the anodic current output of each anodic reference dipole 24 by a respective anodic load, and to the input of cathodic current of each cathode reference dipole 26 by a respective cathode charge.

Finally, the reference terminal 31 is intended to be connected, via a corresponding reference contact, to a predetermined zone of the patient forming a potential reference.

Thanks to such a reference terminal 31, and once the reference contact is connected to the patient, an equipotential, that is to say a potential common to the implantable medical device 6 and to the human body, is defined. This way any floating voltage is removed.

Architecture of the Current Amplifier 22

The architecture of the current amplifier 22 will now be described with reference to FIGS. 6 to 8.

Figure 6:
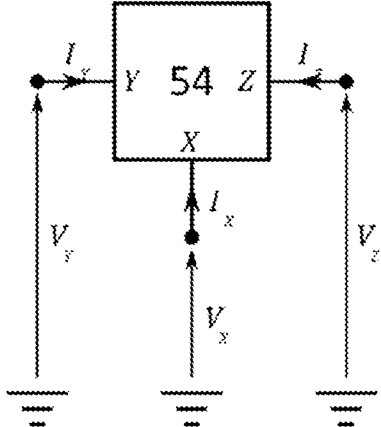
FIG. 6 is a schematic representation of a current conveyor implemented in the current distributor of FIG. 5.

Preferably, the current amplifier 22 comprises at least one current conveyor 54 as illustrated in FIG. 6. Such a current conveyor 54 includes a current input port X, a voltage input port Y and a current output port Z.

More preferably, the current conveyor 54 is a second-generation current conveyor having an operation governed by the relation:

$$\begin{pmatrix} I_Y \\ V_X \\ I_Z \end{pmatrix} = \begin{pmatrix} 0 & 0 & 0 \\ 1 & 0 & 0 \\ 0 & -1 & 0 \end{pmatrix} \begin{pmatrix} V_Y \\ I_X \\ V_Z \end{pmatrix}$$

where $I_X$, $I_Y$ and $I_Z$ are respectively currents injected into the current input port voltage Y and current output port Z; and $V_X$, $V_Y$ and $V_Z$ are voltages between, on the one hand, respectively, the current input port X, the voltage input port Y and the current output port Z, and, on the other hand, a reference point presenting a predetermined electric potential.

The use of a second-generation current conveyor is advantageous, insofar as the value of the current $I_Y$ is zero, which simplifies the design of the current amplifier 22.

For example, each current conveyor 54 is a metal-oxide gated field effect transistor whose source forms the current input port X, the gate forms the voltage input port Y and the drain forms the current output port Z.

Figure 7:
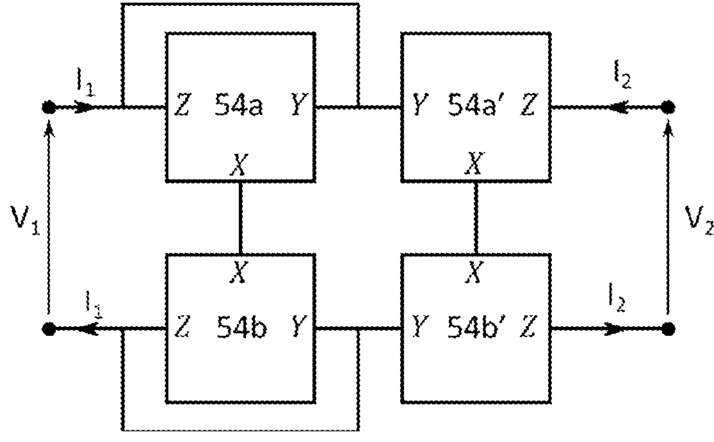
FIG. 7 is a schematic representation of a first embodiment of a current amplifier of the current distributor of FIG. 5.

According to a preferred embodiment, illustrated by FIG. 7, the current amplifier 22 comprises a first current conveyor 54*a*, a second current conveyor 54*a*', a third current conveyor 54*b*' and a fourth current conveyor 54*b*.

In this case, the first current conveyor 54*a* and the second current conveyor 54*a*' are identical. Furthermore, the third current conveyor 54*b*' and the fourth current conveyor 54*b* are identical. Furthermore, and as appears in the figure:

- the current input port X of the first current conveyor 54*a* is connected to the current input port X of the fourth current conveyor 54*b;*
- the current input port X of the second current conveyor 54*a*' is connected to the current input port X of the third current conveyor 54*b';*
- the current output port Z of the first current conveyor 54*a*, the voltage input port Y of the first current conveyor 54*a* and the voltage input port Y of the second current conveyor 54*a*' are connected to each other; and
- the current output port Z of the fourth current conveyor 54*b*, the voltage input port Y of the fourth current conveyor 54*b* and the voltage input port Y of the third current conveyor 54*b*' are connected to each other.

In addition, this circuit is connected as follows to the inputs and outputs of the current amplifier 22:

- the current output port Z of the first current conveyor 54*a* is connected to the primary input terminal 22E1;
- the current output port Z of the fourth current conveyor 54*b* is connected to the primary output terminal 22S 1;
- the current output port Z of the second current conveyor 54*a*' is connected to the secondary input terminal 22E2; and
- the current output port Z of the third current conveyor 54*b*' is connected to the secondary output terminal 22S2.

Such an architecture has the advantage of being symmetrical between the inputs and outputs.

Figure 8:
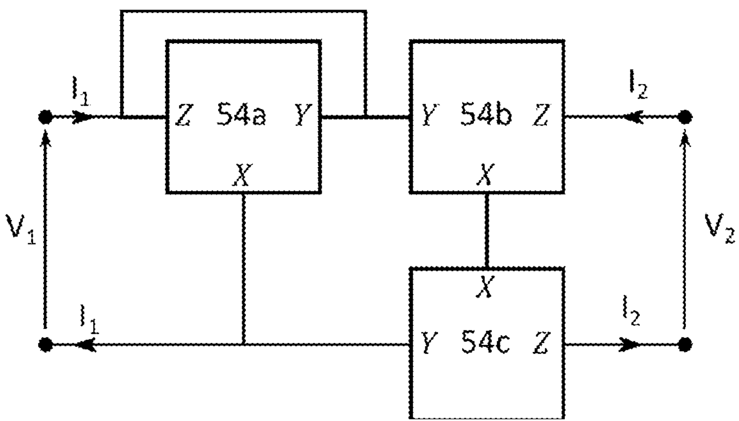
FIG. 8 is a schematic representation of a second embodiment of the current amplifier of the current distributor of FIG. 5.

Another possible architecture for the current amplifier 22 is illustrated by FIG. 8.

In this case, the current amplifier 22 comprises a first current conveyor 54*a*, a second current conveyor 54*b* and a third current conveyor 54*c*.

As it appears in the figure:

- the current input port X of the first current conveyor 54*a* is connected to the voltage input port Y of the third current conveyor 54*c;*
- the current output port Z of the first current conveyor 54*a*, the voltage input port Y of the first current conveyor 54*a* and the voltage input port Y of the second current conveyor 54*b* are connected to each other;
- the current input port X of the second current conveyor 54*b* is connected to the current input port X of the third current conveyor 54*c*; and
- the current output port Z of the first current conveyor 54*a*, the voltage input port Y of the first current conveyor 54*a* and the voltage input port Y of the second current conveyor 54*b* are connected to each other.

In this case, the second predetermined coefficient $H_{12}$ (i.e. the current amplifier gain) is equal to 1. In addition, the first predetermined coefficient $H_{11}$ is 0.

Furthermore, this circuit can be connected in two different ways to the inputs and outputs of the current amplifier 22.

For example:

- the current output port Z of the first current conveyor 54*a* is connected to the primary input terminal 22E1;
- the voltage input port Y of the third current conveyor 54*c* is connected to the primary output terminal 22S 1;
- the current output port Z of the second current conveyor 54*b* is connected to the secondary input terminal 22E2; and
- the current output port Z of the third current conveyor 54*c* is connected to the secondary output terminal 22S2.

Alternatively:

- the voltage input port Y of the third current conveyor 54*c* is connected to the primary input terminal 22E1;
- the current output port Z of the first current conveyor 54*a* is connected to the primary output terminal 22S 1;
- the current output port Z of the third current conveyor 54*c* is connected to the secondary input terminal 22E2; and
- the current output port Z of the second current conveyor 54*b* is connected to the secondary output terminal 22S2.

Functioning

The operation of the neurostimulation system 1 will now be described.

Firstly, the stimulation electrodes are connected to specific nerves of the patient, so that each contact 12 is applied to a corresponding nerve or a predetermined area of a corresponding nerve. Additionally, command sequences are recorded in controller 4. These command sequences relate to profiles of anodic gains, cathodic gains and set current to be implemented to achieve, for example, a predetermined motor function.

When neurostimulation of all or part of the nerves to which the contacts 12 are connected is required, the controller 4 sends to the sequencer 9 of the implantable medical device the command sequence corresponding to the neurostimulation sought.

In this case, the sequencer 9 controls both the current generator 14 and the anodic and cathodic current sources 34, 36 of the current distributor 10 so that:

- during a stimulation time window, the set current is injected between the primary input terminal 22E1 and the primary output terminal 22S1 of the current amplifier 22, the anodic gain $K_a$ of at least one first stimulation bridge 28 being non-zero, and the cathodic gain $K_c$ of at least one second stimulation bridge 28 being non-zero; and
- during a return to equilibrium time window subsequent to the stimulation time window, the set current is injected between the primary input terminal 22E1 and the primary output terminal 22S 1 of the current amplifier 22, the anodic gain $K_a$ of at least a third stimulation bridge being non-zero, and the cathodic gain $K_c$ of at least a fourth stimulation bridge being non-zero.

More specifically, the stimulation time window and the return to equilibrium time window are consecutive and distinct from each other.

Furthermore, the integral of the total current flowing between the positive power bus 18 and the negative power bus 20 during the stimulation time window is equal to the integral of the total current during the time window for return to equilibrium.

For example, if the current switcher 16 includes only two stimulation bridges, the fourth stimulation bridge is the first stimulation bridge, and the third stimulation bridge is the second stimulation bridge.

The invention claimed is:

1. A current switcher for neural stimulation current distributor, the current switcher comprising:

- a positive power bus intended to be connected to a positive power source, and a negative power bus intended to be connected to a negative power source;
- a floating output current amplifier comprising, on the one hand, a primary input terminal and a primary output terminal, and, on the other hand, a secondary input terminal and a secondary output terminal, the floating output current amplifier being configured to circulate, between the secondary input terminal and the secondary output terminal, an intermediate current depending on a set current circulating between the primary input terminal and the primary output terminal;

at least one anodic reference dipole comprising an anodic current input connected to the positive power bus and an anodic current output connected to the secondary input terminal of the floating output current amplifier;

at least one cathode reference dipole comprising a cathodic current input connected to the secondary output terminal of the floating output current amplifier, and a cathodic current output connected to the negative power bus; and at least two stimulation bridges, each stimulation bridge comprising:

a stimulation port;

an anodic current source connected between the positive power bus and the stimulation port, and configured to copy, with a respective anodic gain, the intermediate current passing through an anodic reference dipole associated among the at least one anodic reference dipole; and a cathodic current source connected between the stimulation port and the negative power bus, and configured to copy, with a respective cathode gain, the intermediate current passing through a cathode reference dipole associated among the at least one cathode reference dipole.

2. The current switcher according to claim 1, wherein the floating output current amplifier is a current-balanced non-reciprocal quadrupole configured such that the intermediate current is related to the set current by a proportionality relationship.

3. The current switcher according to claim 2, wherein the proportionality relationship is:

$$\begin{pmatrix} V_1 \\ I_2 \end{pmatrix} = \begin{pmatrix} H_{11} & 0 \\ H_{12} & 0 \end{pmatrix} \begin{pmatrix} I_1 \\ V_2 \end{pmatrix}$$

where $V_1$ is a voltage between the primary input terminal and the primary output terminal;

$V_2$ is a voltage between the secondary input terminal and the secondary output terminal;

$I_1$ is the set current;

$I_2$ is the intermediate current;

$H_{11}$ is a first predetermined coefficient, homogeneous with a resistance; and $H_{12}$ is a second predetermined, dimensionless coefficient.

4. The current switcher according to claim 2, wherein the floating output current amplifier comprises at least one current conveyor comprising a current input port, a voltage input port and a current output port.

5. The current switcher according to claim 4, wherein the current conveyor is a second generation current conveyor having an operation governed by the relation:

$$\begin{pmatrix} I_Y \\ V_X \\ I_Z \end{pmatrix} = \begin{pmatrix} 0 & 0 & 0 \\ 1 & 0 & 0 \\ 0 & -1 & 0 \end{pmatrix} \begin{pmatrix} V_Y \\ I_X \\ V_Z \end{pmatrix}$$

where $I_X$, $I_Y$ and $I_Z$ are respectively currents injected into the input port of current, voltage input port and current output port; and $V_X$, $V_Y$ and $V_Z$ are voltages between, on the one hand, respectively, the current input port, the voltage input port and the current output port, and, on the other hand, a reference point having a predetermined electric potential.

6. The current switcher according to claim 5, in which each current conveyor is a metal-oxide gate field effect transistor whose source forms the current input port, the gate forms the voltage input port and drain forms the current output port.

7. The current switcher according to claim 5, wherein the floating output current amplifier comprises a first current conveyor, a second current conveyor, a third current conveyor and a fourth current conveyor, the first current conveyor and the second current conveyor being identical, the third current conveyor and the fourth current conveyor being identical, the current input port of the first current conveyor being connected to the current input port of the fourth current conveyor, the current input port of the second current conveyor being connected to the current input port of the third current conveyor, the current output port of the first current conveyor, the voltage input port of the first current conveyor and the voltage input port of the second current conveyor being connected to each other, the current output port of the fourth current conveyor, the voltage input port of the fourth current conveyor and the voltage input port of the third current conveyor are connected to each other, the current output port of the first current conveyor is connected to the primary input terminal of the floating output current amplifier, the current output port of the fourth current conveyor being connected to the primary output terminal of the floating output current amplifier, the output port of the second current conveyor being connected to the secondary input terminal of the floating output current amplifier, and the current output port of the third current conveyor being connected to the secondary output terminal of the floating output current amplifier.

8. The current switcher according to claim 5, wherein the floating output current amplifier comprises a first current conveyor, a second current conveyor and a third current conveyor, the current input port of the first current conveyor being connected to the voltage input port of the third current conveyor, the current output port of the first current conveyor, the voltage input port of the first current conveyor and the voltage input port of the second current conveyor being connected to each other, the current input port of the second current conveyor being connected to the current input port of the third current conveyor, the current output port of the first current conveyor, the voltage input port of the first current conveyor and the voltage input port of the second current conveyor being connected to each other, the first predetermined coefficient $H_{11}$ being equal to 0, the second predetermined coefficient $H_{12}$ being equal to 1, and:

the current output port of the first current conveyor being connected to the primary input terminal of the floating output current amplifier, the voltage input port of the third current conveyor being connected to the primary output terminal of the floating output current amplifier, the current output port of the second current conveyor being connected to the secondary input terminal of the floating output current amplifier, and the current output port of the third current conveyor being connected to the secondary output terminal of the floating output current amplifier, or the voltage input port of the third current conveyor being connected to the primary input terminal of the current amplifier with floating output, the current output port of the first current conveyor being connected to the primary output terminal of the floating output current amplifier, the current output port of the third current conveyor being connected to the secondary input terminal of the floating output current amplifier, and the current output port of the second current conveyor being connected to the secondary output terminal of the floating output current amplifier.

9. The current switcher according to claim 1, also comprising a reference terminal intended to be connected, on the one hand, between the positive power source and the negative power source, and, on the other hand, to a potential reference, the reference terminal being, in addition, connected to the anodic current output of each anodic reference dipole by a respective anodic load, and to the cathodic current input of each cathode reference dipole by a respective cathodic load.

10. The current switcher according to claim 1, in which, for each stimulation bridge:

the corresponding anodic reference dipole comprises a first anode transistor, and the corresponding anodic current source comprises at least one second anode transistor, each second anode transistor being connected to the first anode transistor for defining, with the first anode transistor, a current mirror; and the corresponding cathode reference dipole comprises a first cathode transistor, and the corresponding cathodic current source comprises at least one second cathode transistor, each second cathode transistor being connected to the first cathode transistor to define, with the first cathode transistor, a current mirror.

11. The current switcher according to claim 1, in which, for each stimulation bridge:

the corresponding anodic current source comprises at least one anodic elementary source connected between the positive power bus and the stimulation port, each anodic elementary source comprising a second anode transistor in series with an anodic switching member; and/or the corresponding cathodic current source comprises at least one cathodic elementary source connected between the stimulation port and the negative power bus, each cathodic elementary source comprising a second cathode transistor in series with a cathodic switching member, the value of the anodic gain being a function of an on or off state of each anodic switching member, and/or the value of the cathodic gain being a function of an on or off state of each cathodic switching member.

12. The current switcher according to claim 11, in which, for each stimulation bridge:

the corresponding anodic current source comprises a plurality of anodic elementary sources connected in parallel between the positive power bus and the stimulation port; and/or the corresponding cathodic current source comprises a plurality of cathodic elementary sources connected in parallel between the stimulation port and the negative power bus.

13. A neural stimulation current distributor comprising the current switcher according to claim 1, and a programmable current generator connected between the primary input terminal and the primary output terminal of the floating output current amplifier, the programmable current generator being configured to deliver the set current according to a command applied to it.

14. An implantable medical device comprising the neural stimulation current distributor according to claim 13, a sequencer, and a plurality of contacts each connected to a respective stimulation port, the sequencer being configured to control, according to a received command sequence associated with a corresponding neurostimulation, each anodic current source, respectively each cathodic current source, to set the value of the corresponding anodic gain, respectively the corresponding cathodic gain, so that, at each instant:

for each stimulation bridge, one of the corresponding anodic gain and cathodic gain is zero; and the sum of the anodic gains and the sum of the cathodic gains, taken over all the stimulation bridges, are equal.

15. The implantable medical device according to claim 14, further comprising a receiver connected to the input of the sequencer, the receiver being configured to receive the command sequence, and to transmit the received command sequence to the sequencer.

16. The implantable medical device according to claim 14, in which the sequencer is configured to control each anodic current source and each cathodic current source, as a function of the set current, so that:

the integral of a total current circulating between the positive power bus and the negative power bus during a stimulation time window is equal to the integral of the total current during a time window for returning to equilibrium, the stimulation time window and the time window for returning to equilibrium being consecutive and distinct from each other; and the anodic gain of at least one anodic current source, respectively the cathodic gain of at least one cathodic current source, has a zero value during one of the stimulation time window and the time window for return to equilibrium, and a non-zero value during the other among the time window of stimulation and the time window for return to equilibrium.

17. The implantable medical device according to claim 14, in which the sequencer is, furthermore, configured to control the programmable current generator in order to deliver the set current according to the received command sequence.

18. The implantable medical device according to claim 14, in which, for each stimulation bridge:

the corresponding anodic current source comprises at least one anodic elementary source connected between the positive power bus and the stimulation port, each anodic elementary source comprising a second anode transistor in series with an anodic switching member; and/or the corresponding cathodic current source comprises at least one cathodic elementary source connected between the stimulation port and the negative power bus, each cathodic elementary source comprising a second cathode transistor in series with a cathodic switching member, the sequencer being configured to control, depending on the command sequence, an on or off state of each anodic switching member to set the value of the anodic gain, and/or to control an on or off state of each cathodic switching member to set the value of the cathodic gain.

19. A neurostimulation system comprising the implantable medical device according to claim 14 and a controller configured to determine each command sequence, and to transmit each determined command sequence to the implantable medical device.

20. A neuro-stimulation method implemented by means of the implantable medical device according to claim 14, the neuro-stimulation method comprising the steps:

during a stimulation time window, injection of the set current between the primary input terminal and the primary output terminal of the floating output current amplifier, the anodic gain of at least one first stimulation bridge being non-zero, and the cathodic gain of at least one second stimulation bridge being non-zero; and during a time window for returning to equilibrium, injection of the set current between the primary input terminal and the primary output terminal of the floating output current amplifier, the anodic gain of at least a third stimulation bridge being non-zero, and the cathodic gain of at least a fourth stimulation bridge being non-zero, and the integral of a total current circulating between the positive power bus and the negative power bus during the stimulation time window being equal to the integral of the total current during the time window for return to equilibrium, the stimulation time window and the time window for returning to equilibrium being consecutive and distinct from each other.

* * * * *